United States Patent
Olszewski et al.

(10) Patent No.: US 8,629,293 B2
(45) Date of Patent: Jan. 14, 2014

(54) PROCESS FOR THE PREPARATION OF FE(III) CHELATES OF N,N'-DI(2-HYDROXYBENZYL)-ETHYLENEDIAMINE-N,N'-DIACETIC ACID AND ITS DERIVATIVES

(75) Inventors: Radoslaw Olszewski, Poznan (PL); Adam Nawrocki, Poznan (PL); Filip Stefaniak, Ostrzeszow (PL); Joanna Ewa Stegient-Nowicka, Poznan (PL); Juan Jose Lucena Marotta, Madrid (ES)

(73) Assignee: Przedsiebiorstwo Produkcyjno-Consultingowe Adob SP. Z O.O. SP. K., Poznan (PL)

( * ) Notice: Subject to any disclaimer, the term of this patent is extended or adjusted under 35 U.S.C. 154(b) by 154 days.

(21) Appl. No.: 13/382,695

(22) PCT Filed: Jul. 1, 2010

(86) PCT No.: PCT/EP2010/059363
§ 371 (c)(1), (2), (4) Date: Jan. 6, 2012

(87) PCT Pub. No.: WO2011/006763
PCT Pub. Date: Jan. 20, 2011

(65) Prior Publication Data
US 2012/0108835 A1  May 3, 2012
US 2012/0271062 A9  Oct. 25, 2012

(30) Foreign Application Priority Data
Jul. 17, 2009 (EP) .................................... 09461511

(51) Int. Cl.
*C07F 15/02* (2006.01)
(52) U.S. Cl.
USPC ......................................................... 556/148
(58) Field of Classification Search
USPC ......................................................... 556/148
See application file for complete search history.

(56) References Cited

U.S. PATENT DOCUMENTS

| 3,038,793 A | 6/1962 | Kroll et al. |
| 3,758,540 A | 9/1973 | Martell |

FOREIGN PATENT DOCUMENTS

| EP | 0694528 A | 1/1996 |
| GB | 843003 A | 8/1960 |
| GB | 1397479 A | 6/1975 |
| WO | WO99/37602 A | 7/1999 |

*Primary Examiner* — Porfirio Nazario Gonzalez
(74) *Attorney, Agent, or Firm* — Fish & Richardson P.C.

(57) ABSTRACT

The invention relates to the process for the preparation of iron(III) chelates of N,N'-di(2-hydroxybenzyl)ethylenediamine-N,N'-diacetic acid and its derivatives of the formula (I) wherein both R substituents have the same meaning and represent H, $C_1$-$C_4$ alkyl, $CH_2OH$, $SO_3M$ or COOM, and M is a sodium, potassium or ammonium cation, wherein the aqueous solution of a corresponding chelating agent is contacted with metallic iron by the circulation of said aqueous solution through the bed of pieces of metallic iron in a flow reactor while simultaneously blowing air or oxygen through the aqueous solution of the chelating agent in the flow reactor, optionally in the presence of a hydrogen peroxide solution. Chelates of the formula (I) are useful as the components of plant fertilizers.

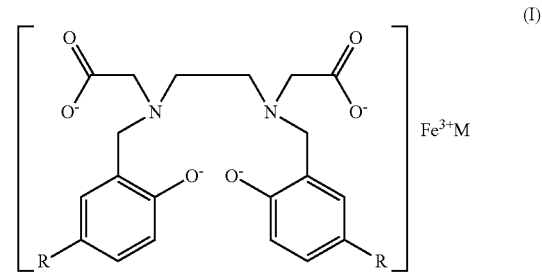

23 Claims, 2 Drawing Sheets

US 8,629,293 B2

PROCESS FOR THE PREPARATION OF FE(III) CHELATES OF N,N'-DI(2-HYDROXYBENZYL)-ETHYLENEDIAMINE-N,N'-DIACETIC ACID AND ITS DERIVATIVES

CROSS REFERENCE TO PRIOR APPLICATIONS

This is a U.S. National Phase application under 35 U.S.C. §371 of International Patent Application No. PCT/EP2010/059363, filed Jul. 1, 2010, and claims the priority of European Patent Application No. 09461511.9, filed Jul. 17, 2009 both of which are incorporated by reference herein. The International Application published in English on Jan. 20, 2011 as WO 2011/006763 under PCT Article 21(2).

THE FIELD OF THE INVENTION

The present invention relates to a process for the preparation of Fe(III) chelates of N,N'-di(2-hydroxybenzyl)ethylenediamine-N,N'-diacetic acid and its derivatives, in particular derivatives substituted at the phenyl group. More specifically, the invention relates to a process for the preparation of Fe(III) chelates of alkaline salts of N,N'-di(2-hydroxybenzyl)ethylenediamine-N,N'-diacetic acid and its derivatives.

THE STATE OF THE ART

The Fe(III) chelates of N,N'-di(2-hydroxybenzyl)ethylenediamine-N,N'-diacetic acid, known also under the abbreviation HBED, as well as its derivatives substituted at position 5 of the phenyl ring with a carboxy, alkyl, sulphonyl or hydroxymethyl group, are useful as components of the mineral fertilizers for correcting iron deficiencies in hydroponic, fertigation, and soil cultivations. In particular, they find application in the case of a limestone soil having a very high pH value as well as a high concentration of hydrogencarbonates. Due to their high stability constants, they are the desired alternative to the commonly used iron chelates of ethylenediamine-N,N'-di[(ortho-hydroxyphenyl)acetic acid] (o,oEDDHA), ethylenediamine-N,N'-di[(ortho-hydroxymethylphenyl)acetic acid] (o,oEDDHMA), and ethylenediamine-N,N'-di[(2-hydroxy-5-sulphophenyl)acetic acid] (EDDHSA).

Preparation of alkaline salts of iron chelates of HBED and its derivatives substituted at position 5 of the phenyl ring with methyl or sulphonyl group was described in U.S. Pat. No. 3,038,793. One of the processes described therein consists in direct addition of an aqueous solution of the iron salt ($FeCl_3$) to an aqueous solution of the chelating compound—HBED or its derivative—in the presence of a base such as sodium hydroxide. The chelate is obtained in the form of an aqueous solution, from which it is isolated by evaporation to dryness. As an alternative process for the chelate preparation, a reaction of the chelating compound in the acid form with a freshly precipitated iron hydroxide is mentioned, without describing this process in more detail.

U.S. Pat. No. 3,758,540 describes three processes for the preparation of iron chelates of the substituted N-(2-hydroxybenzyl)aminopolycarboxylic acids. The process described as the preferred and simplest one is the reaction of N-(2-hydroxybenzyl)aminopoly-carboxylic acid in its free acid form with ferric hydroxide in an aqueous medium, optionally with the addition of an alkaline metal hydroxide. Ferric hydroxide must be freshly precipitated from an aqueous solution of a ferric salt, such as $FeCl_3$, by adding an aqueous solution of a base, preferably ammonium hydroxide, and the chelate formation reaction itself is carried out at reflux and needs a dozen or so hours to completion. The final product is isolated by concentration and drying of the aqueous reaction solution. As an alternative, a process is mentioned that consists in the preparation of an aqueous solution of a ferric salt such as chloride, nitrate, acetate or carbonate, followed by the reaction with a chelating agent in the acid form, alkalizing with ammonium hydroxide and evaporation of the obtained chelate solution to dryness. The third of the described processes consists in the preparation of an aqueous solution of the ferric salt of a mineral acid, followed by reaction with an equimolar amount of a chelating agent sodium salt, and evaporation of thus obtained solution of the ferric chelate to dryness.

The processes employing iron salts have several steps and generate the stoichiometrical amounts of the corresponding inorganic anions of these salts (e.g., chloride, sulphate, nitrate), that are production wastes or impurities in the final product. These impurities additionally significantly reduce the water solubility of the chelates, that is already relatively low in the case of chelates containing a phenol group in their molecules. The use of a carbonate iron salt causes problems with effervescence due to carbon dioxide generation. Furthermore, the chelates are obtained in the form of aqueous solutions that require the labour- and energy-consuming evaporation of water in order to obtain the product in the solid form.

As a solution of the problem of generating stoichiometric amounts of inorganic salts formed in the reaction of a chelating compound with an iron salt, a process consisting in the reaction of an aminopolycarboxylic acid with metallic iron in the presence of an oxidant (air, oxygen or an aqueous solution of hydrogen peroxide) was proposed in the prior art.

Such a process is described in GB1397479 for the preparation of iron chelates of aliphatic aminopolycarboxylic acids such as, e.g., EDTA, and consists in dissolving particulate metallic iron having a well developed surface, i.e. in the form of a powder, flakes, wool or a fine wire of the diameter not greater than 1 mm, in an aqueous solution of an aminopolycarboxylic acid with simultaneous oxidation of iron with oxygen and hydrogen peroxide. The process should be carried out in the presence of soluble iron salts or its chelates, to promote the dissolution of metallic iron and its reactivity with the chelating agent, what results in the presence of salts of the introduced anions in the final product.

The use of metallic iron in the powder form in the presence of oxygen or a hydrogen peroxide solution as an oxidant is also described in EP 0694528A2 for the preparation of iron chelates of alkylenediamine-N,N'-disuccinic acids.

The use of metallic iron in the presence of ammonia at the slight excess of iron with respect to chelating agent for the preparation of iron chelates of alkylenediamine-N,N'-polyacetic acids is also mentioned, although not exemplified in any working example, in WO99/37602.

In the known processes employing metallic iron, the ratio of iron to chelating agent is close to the stoichiometric one or a slight excess of the chelating agent is used. Because of that, the reaction rate slows down with the time and there is a serious risk that not all chelating agent will be reacted. A modification of these known processes by using the excess of particulate metallic iron could pose problems with the removal of the remaining unreacted iron from the reaction mixture, especially in the case of using a finely powdered iron dust. Moreover, carrying out the reaction in the batch mode, in a mixing tank, as proposed in the state of the art, could result in formation of froth when air is bubbled through the reaction solution, this making the technological operation difficult.

In the known processes using metallic iron, the product is obtained in the form of an aqueous solution. This liquid form is not always convenient in the case of commercial preparations for the fertilizers applications, since transportation of the final product to the end users is a significant cost and operational burden due to the product volume. Furthermore, because of the liquid form of the final product it is impossible to add the chelate to solid fertilizer compositions. The commercial form required for application in agriculture is usually a solid form to be diluted by the end user. To achieve this, the obtained aqueous solution should be concentrated, this resulting in an increase in the labour and energy consumption of the process, being the greater the more diluted is the aqueous solution.

These technical problems are even more important in the case of the preparation of Fe chelates with the chelating agents containing phenol groups in their molecules, such as HBED and its derivatives substituted at position 5 of the phenyl ring. In the prior art processes the concentrations of aliphatic chelating agents in water as high as in the range of 30-50% by weight can be reached, and a similar concentration range of the final water-soluble chelate can be achieved as well. However, salts of HBED itself and of its derivatives, as well as their corresponding Fe(III) chelates are significantly less water soluble compared to the alkyleneaminopolycarboxylic acids without phenolic groups. As a consequence, the reaction with metallic iron should be carried out in a larger amount of water to obtain dissolution of both the starting chelating agent and the final chelate. This would result in the need of removing a large amounts of water during concentration of the product, if solid form is desired. For example, if the starting material for chelation is the chelating agent in the monohydrochloride form, then in the case of HBED and its derivatives the precipitation of the chelate from the saturated solution starts after exceeding the concentration of 10-11% by weight of the chelate in the sodium or potassium form and 14-15% by weight of the chelate in the ammonium form. When these concentrations are exceeded, the reaction medium turns into the saturated chelate solution/chelate precipitate system. Furthermore, an additional technical problem that limits the possibility of carrying out the reaction at the excess of iron, especially with iron in the particulate form, is that chelates of HBED and its derivatives, unlike the chelates of alkyleneaminopolycarboxylic acids such as EDTA, the preparation of which was described in GB1397479 and EP 0694528A2, form amorphous and sticky solids rather than precipitate from the aqueous solution in the crystalline form. Thus, this low solubility may result in easily exceeding the water solubility, precipitation of the product and sticking it to the particulate iron used in the processes described in the prior art.

Due to the beneficial properties of Fe(III)HBED chelates and its derivatives, there is still a need for a technologically simple, efficient and cost-effective process for the preparation of alkaline salts of Fe(III) chelates HBED and its derivatives 5-substituted in the phenol ring, suitable for an industrial scale, and providing the product of as low content of other anions as possible, and also in the preferred solid form.

The technical problems discussed above have been solved by the process according to the invention, consisting in carrying out the reaction of a chelating agent in an aqueous solution with metallic iron in the form of a bed of iron pieces in a flow reactor, in the presence of an oxidant.

The process according to the invention may be used for the preparation of both the aqueous solution of the chelate and, in the preferred embodiment, the chelate in the solid form without need of concentration of diluted aqueous solution of that chelate.

DETAILED DESCRIPTION OF THE INVENTION

The present invention relates to a process for the preparation of iron(III) chelates of N,N'-di(2-hydroxybenzyl)ethylenediamine-N,N'-diacetic acid and its derivatives of the formula (I)

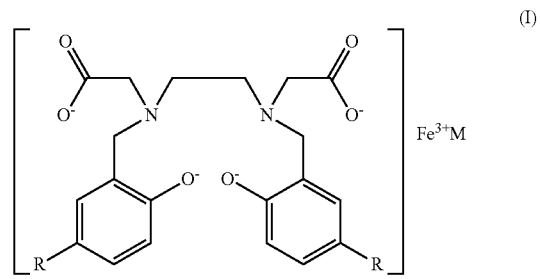

wherein both substituents R have the same meaning and represent H, $C_1$-$C_4$ alkyl, $CH_2OH$, $SO_3M$ or COOM, and M is a sodium, potassium or ammonium cation, which process is characterized in that a starting aqueous solution of a chelating agent of the formula (II)

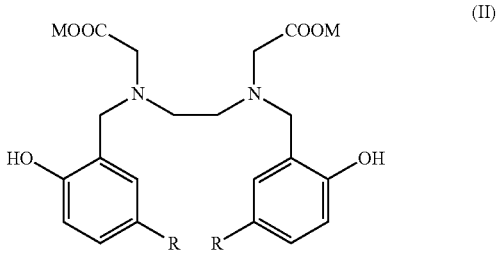

wherein R and M are as defined above is prepared, the aqueous solution is contacted with metallic iron by circulation of said aqueous solution through the bed of pieces of metallic iron in a flow reactor while simultaneously blowing air or oxygen through the aqueous solution of the chelating agent in the flow reactor, and a hydrogen peroxide solution is optionally added to the aqueous solution of the chelating agent received from the flow reactor and before returning it to the flow reactor, whereby said circulating aqueous solution is continuously enriched with the iron chelate of the formula (I).

Throughout this specification, the circulating aqueous solution of a chelating agent, to which optionally a hydrogen peroxide solution is continuously added, and which is enriched with the prepared chelate, is named also the working solution. One should understand that both these terms, i.e. "the aqueous solution of a chelating agent" and "a working solution", may be used interchangeably throughout this specification.

Air or oxygen play a role of an oxidant of iron and are provided to the reaction medium by blowing, like bubbling, through the aqueous solution of a chelating agent while it passes through the flow reactor.

Additionally, blowing air or oxygen through the reaction medium results in its agitation, and this prevents precipitation of the formed chelate in dead spaces of the bed and leads to uniform conversion in the whole volume of the bed in the reactor.

Preferably, besides air or oxygen, an aqueous solution of hydrogen peroxide at a concentration in the range of 3 to 60% by weight may be used, as a second oxidant, in the process according to the invention. The aqueous solution of hydrogen peroxide is provided in the aqueous solution of the chelating agent (the working solution) and added to the working solution after it leaves the flow reactor and before returning it to the flow reactor. Preferably, the concentration of hydrogen peroxide is 50% by weight.

In the preferred embodiment a combined oxidation is used, i.e., either with hydrogen peroxide solution and blowing air or using hydrogen peroxide solution and blowing oxygen.

In the preferred embodiment, where a combined oxidation is used, as the hydrogen peroxide solution is consumed, its amount in the circulating aqueous solution (the working solution) is replenished after receiving it from the flow reactor and before returning it to the flow reactor.

Air or oxygen is fed to the flow reactor at a volume rate of from 1 to 40 $m^3$ of air/h or from 0.25 to 13 $m^3$ of oxygen/h. The feed rates of the hydrogen peroxide solution, and the feed rates of oxygen or air depend on the amounts of the starting materials introduced into the chelation reaction as well as the concentration of the starting chelating agent. An amount of the hydrogen peroxide solution is adjusted so that to provide the chelating agent:oxidant ratio of 1:2-6, under assumption that the iron:chelating agent ratio in the final product is 1:1.2, preferably 1:1.

Feeding the total amount of the hydrogen peroxide solution is distributed over time in such a manner that feeding should take place over a time from 8 to 20 hours, preferably from 10 to 14 hours at a constant feed rate.

Depending on the concentration the chelating agent in the starting aqueous solution circulating through the bed of metallic iron, iron chelate of the Formula (I) may be obtained in the form of an aqueous solution or a solid product.

Therefore, in a first embodiment of the process according to the invention, the iron chelate product of the formula (I) is manufactured in the form of an aqueous solution.

According to the first embodiment, a concentration of the starting aqueous solution of the chelating agent is in the range of 1 to 12% by weight, and the circulation of the aqueous solution of the chelating agent (the working solution) is carried out until complete conversion of the chelating agent in the aqueous solution, whereby the aqueous solution of the iron chelate of formula (I) is produced as a final product.

The starting concentration of the chelating agent is adjusted so that not to exceed the limit of solubility of the obtained chelate in the circulating solution and not to cause its precipitation.

During the circulation of the aqueous solution of the chelating agent, due to the reaction and corresponding consumption of the chelating agent, the concentration of the iron chelate product in the circulating working solution increases until the state of saturation of the aqueous solution with the chelate is reached.

By terminating circulation of the aqueous solution just after reaching the state of saturation with the chelate, the aqueous chelate solution is obtained, that may be the final product itself or may be evaporated to obtain the solid product, depending on the envisaged use.

Reaching the state of saturation (complete conversion of the chelating agent) is determined by regularly monitoring the iron concentration in the circulating aqueous solution, after receiving it from the flow reactor, and before returning it to the process. The state of saturation is considered to be reached when the iron concentration is not changing, i.e., there is no increase in its concentration, for a certain period of time.

Alternatively, reaching the state of saturation may be determined by regularly monitoring the chelating agent concentration in the working solution. This concentration may be monitored, for example, by HPLC (high-performance liquid chromatography), as it is well known to the persons skilled in the art. The circulation of the working solution is stopped after obtaining a constant drop of the chelating agent concentration below the predetermined value, or when no significant drop of the concentration is observed for a certain period of time.

After terminating the circulation, the aqueous solution is the final product—the solution having a high iron concentration, that may be used as such.

Subsequently, another starting solution of the chelating agent may be prepared and the next process cycle may be carried out according to the first embodiment of the process.

As it will appreciated by a person skilled in the art, the aqueous solution may also be concentrated by evaporation of water so that to obtain the solid product, if desired.

In a second embodiment of the process according to the invention, the iron chelate product is manufactured in a solid form.

According to the second embodiment, a concentration of the starting aqueous solution of the chelating agent is in the range of 12 to 25% by weight, the circulation of the aqueous solution is carried out until oversaturation of the circulating aqueous solution with the iron chelate is reached, whereby a solid iron chelate precipitates in the circulating solution received from the flow reactor and is separated from the working solution in a sedimentation tank and collected therein, the circulating aqueous solution is optionally fed with the chelating agent before returning it to the flow reactor, and the collected solid iron chelate precipitate is periodically recovered from the sedimentation tank.

In the second embodiment, the concentration of the starting solution is adjusted so that as the chelating agent reacts, the chelate oversaturation is reached, and the chelate precipitates in the sedimentation tank from the suspension of the chelate in the working solution. Furthermore, unlike in the first embodiment in which the circulation is carried out until substantially complete consumption of the chelating agent in the circulating solution, in this second embodiment the loss of the chelating agent due to its reaction may be replenished, if needed, by its continuous feeding into the circulating working solution until the sufficient amount of the precipitate in the sedimentation tank is obtained. In this way, continuous precipitation of the solid chelate is achieved as it is formed. Feeding the chelating agent is carried out so as to keep its concentration in the circulating solution in the range of concentrations such as in the starting solution, under assumption that the concentration of the chelating agent in the working mixture is a sum of the already chelated ligand and the fresh ligand added in a new portion. After receiving the working solution from the flow reactor, the chelate precipitate is separated from the aqueous solution by settling in the sedimentation tank, the separated aqueous solution is optionally replenished with the chelating agent and the hydrogen peroxide solution, and returned to the flow reactor for further reaction.

The separation of the chelate precipitate in the sedimentation tank as it is formed prevents deposition of the precipitate on the metallic pieces, and simultaneously shifts the reaction equilibrium towards the chelate formation.

Preferably, the concentration of the starting solution of the chelating agent ranges from 14 to 17% by weight.

In the second embodiment of the process according to the invention, the circulation of the aqueous solution and optional feeding with the chelating agent is usually carried out until the amount of the iron chelate precipitate equal to 5 to 40% of the volume of the sedimentation tank is collected. Typically, the amount of the iron chelate precipitate is estimated by determination of the height of the precipitate deposit in the sedimentation tank with relation to the upper level of liquid in the sedimentation tank. After collecting such an amount of the precipitate, recovery of the collected precipitate from the sedimentation tank in the form of a solid product is carried out. This amount is determined by practical and economical factors so as to perform the periodical recovery as seldom as possible.

In the case when the chelating agent in the working solution is saturated (i.e., consumed) and the amount of the precipitate collected in the sedimentation tank is not large enough to carry out its recovery, circulation may be carried out further, by making up the working solution with subsequent portions of the chelating agent to obtain the concentration in the range of 12-25% by weight, under assumption that the concentration of the chelating agent in the working mixture is a sum of the already chelated ligand and the fresh ligand added in the new portion, until the amount of precipitate is sufficient for terminating the circulation and recovering the solid precipitate.

Preferably, after collecting 5 to 40% by volume of the iron chelate precipitate in the sedimentation tank and stopping the optional further feeding with the chelating agent, the circulation of the working solution and reaction of the chelating agent with iron is continued until obtaining the concentration of the chelating agent in the circulating solution below 2% by weight.

The periodical recovery of collected the iron chelate precipitate from the sedimentation tank may be carried out, e.g., by filtration or centrifugation.

In the process according to the invention, iron comprising the packing (the bed) of the flow reactor is in the form of pieces such as sheets, plates, wires, strips, rods, slabs, bars, or elements of any shape, such as, e.g., rings or tubes, having the size much greater and the surface much less developed than described in the state of the art. In particular, the term "iron in the form of pieces" is meant to define iron in a form other than powder, dust and fine wool, and having no developed surface. The iron pieces should be loosely packed. The reaction is carried out at a large excess of iron with relation to the chelating agent, at the expense of the less developed surface. As the reaction proceeds and iron is consumed, the amount of iron in the bed of the flow reactor is periodically replenished.

Preferably, the content of heavy metals such as chromium, nickel, lead, cadmium, and carbon in the metallic iron employed in the process according to the invention should be as low as possible. It is preferred to use iron having low content of impurities, below 0.1% by weight, manufactured metallurgically and characterised by high plasticity and purity.

Unlike the periodic processes known from the prior art that are carried out at the stoichiometrical or less than stoichiometrical amount of iron, carrying out the chelation of iron at the excess of metallic iron in a flow reactor by the process according to the invention increases the rate of reaction of the chelating agent with iron.

In the process according to the invention, due to using pieces of metallic iron of low surface and simultaneously increasing the amount of iron in the reactor, compared to the processes according to the prior art, precipitation of the chelation reaction product on the metallic iron during the process is prevented.

Furthermore, a good conversion of the ligand is achieved without any need for using filtration operations to separate unreacted iron.

Thus, as discussed above, the process according to the invention allows to obtain the chelates of the formula (I) both in the form of a diluted aqueous solution as well as in a solid form.

In the preferred embodiment, the process according to the invention yields the chelates in the solid form, being the preferred one for agrochemical applications.

The starting aqueous solution of the chelating agent of the formula (II) can be prepared by dissolving a sodium, potassium or ammonium salt of the formula (II) (where M represents a sodium, potassium or ammonium cation, respectively) in water.

Alternatively, the aqueous solution of the chelating agent can be prepared by dissolving a hydrochloride or sulphate of the acidic form of the chelating agent (i.e., a compound of the formula (II), wherein M is a hydrogen cation) in water with addition of a stoichiometric amount of a suitable hydroxide. However, in such a case, the final product may contain stoichiometric amounts of the chloride or sulphate ions, that remain in the solution after neutralisation of the chloride or sulphate anion with the hydroxide.

The processes for the preparation of the compounds of the formula (II) are well known. In particular, the compounds of the formula (II) may be prepared, for example, by the process described in the publication No. WO2009037235A1, via reductive amination of glyoxalic acid with a corresponding compound unsubstituted at nitrogen atoms with the carboxymethyl group, and isolation of the compound of the formula (II), wherein M represents H, in the form of a free acid, a hydrochloride or sulphate of the free acid, or, optionally, by conversion of the free acid into an alkaline salt by the treatment with a suitable base, e.g., sodium, potassium or ammonium hydroxide, in an amount sufficient to neutralise the acidic groups present in the compound.

In both of its embodiments, the process according to the invention may be carried out as a co-current process, in which the stream of the aqueous solution of the chelating agent (the working solution) and the stream of air or oxygen gas are introduced at the bottom of the reactor and both streams flow in the same direction.

Alternatively, the process according to both embodiments of the invention may be also carried out as a counter-current process, in which the stream of the aqueous solution and the stream of air or oxygen gas flow in opposite directions; the gas stream is introduced at the bottom of the flow reactor, whereas the aqueous solution of the chelating agent is introduced to the flow reactor from the top onto the bed, and received at the bottom of the reactor. In such a counter-current system, the contact of the working solution with iron metal is enhanced.

As discussed above, the invention provides a versatile and technologically simple process of the preparation of the iron chelates that is easily applicable on the industrial scale. The process according to the invention provides the final chelate product free from inorganic anions remaining after neutralisation of the iron salts. Heating of the reaction is not required, decomposition of the chelating agent being thus prevented. The reaction is slightly exothermic and proceeds at the temperatures ranging from 5 to 55° C., preferably from 20 to 55° C. The spontaneous rise of the temperature up to 55° C. is observed due to the exothermic effect when the reaction is carried out in the presence of hydrogen peroxide. There is no froth formation that would otherwise make operating the process difficult. A product having a high concentration of the micronutrient (iron) is obtained following the drying of the liquid product or the solid product recovered by filtration. Due to circulation of the working solution to the reaction, with or without replenishing it with a new portion of the chelating agent, the water consumption is reduced.

An advantage and versatility of the process consists in the possibility of the manufacture of the iron chelate, according to the needs, both in the form of the solution and in the solid form, without necessity for concentrating the aqueous solution. In the process according to the invention, this is achieved by appropriate adjusting the starting concentration of the chelating agent.

BRIEF DESCRIPTION OF THE DRAWINGS

The process of the invention shall be described in more details by reference to the accompanying drawings. However, it should be understood that the process according to the invention is not limited to the particular embodiments presented schematically in the drawings.

In the drawings.

Figure 1:
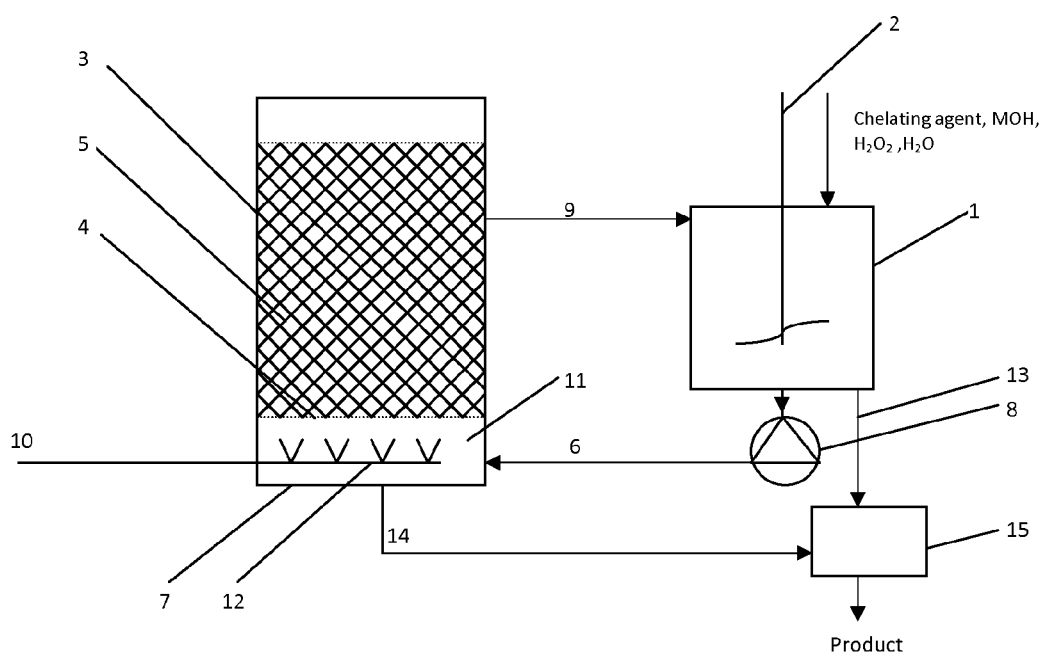
FIG. 1 presents a flowchart of the embodiment of the process according to the invention, carried out in a co-current installation, wherein the product is manufactured in the form of an aqueous solution.

According to the embodiment illustrated in FIG. 1, in which the product is prepared as the aqueous solution, the starting aqueous solution of the chelating agent having the appropriate concentration in the range of 1 to 12% by weight is prepared in a mixing tank 1 equipped with a stirrer 2. For this purpose, the chelating agent in an alkaline salt form, a free acid form, or a hydrochloride or sulphate salt form is placed in the mixing tank 1. To the chelating agent in the alkaline salt form, water is added until complete dissolution. To the chelating agent in the acid form or the hydrochloride or sulphate salt form, water is added along with a stoichiometric amount of sodium, potassium or ammonium hydroxide necessary for complete dissolution of the chelating agent, and sufficient to neutralise the acidic groups present in the starting chelating agent. The concentration of the chelating agent is adjusted depending on the water solubility of the specific chelating agent used so as to obtain a homogeneous solution. The pH value of the solution ranges from 5.5 to 9.

In the flow reactor 3 of the cylindrical column type, made of a chemically resistant material and equipped with a transversely placed perforated baffle or plate 4, a packing consisting of a bed 5 of metallic iron in the form of pieces having a poorly developed surface, i.e., sheets, turnings, slabs, strips, wires, flat bars or profiles is placed. The perforated baffle 4 may be a sieve tray, a grating with an appropriate mesh size, and similar means, providing a rigid and firm support for holding the iron bed and simultaneously allowing the aqueous solution of the chelating agent to flow through the holes in the baffle. An excess of metallic iron with relation to the introduced amount of the chelating agent is used. The previously prepared solution of the chelating agent is fed from the mixing tank 1 through an inlet 6, placed between a bottom 7 of the reactor 3 and the baffle 4, using a circulating pump 8. This solution fills the empty spaces in the iron bed 5 until complete filing the system and reaching the level of an overflow outlet 9, which drains the aqueous solution from the flow reactor. The outlet 9 is located below the upper boundary of the metallic iron bed 5 and connected with the mixing tank 1. After complete filling the system, feeding of compressed air or oxygen starts via a pipe 10 to a space 11 between the bottom 7 of the reactor 3 and the baffle 4, and blowing of the introduced gas in the form of bubbles in the aqueous solution in the reactor by a bubbling means 12 that may be a sparger, a diffuser of any type, such as a tube diffuser, a disc diffuser, a membrane diffuser, a ceramic diffuser, and any similar devices. Simultaneously, feeding the hydrogen peroxide solution into the mixing tank 1 starts if this is to be used.

The aqueous solution of the chelating agent outflows (discharges gravitationally) from the reactor 3 via the outlet 9 to the mixing tank 1. The aqueous solution is thereby received from the flow reactor and reintroduced into the mixing tank 1, where it is replenished with the hydrogen peroxide solution, if necessary, and also homogenised by mixing.

As iron in the bed 5 is consumed, its amount is also periodically replenished.

The circulation of the working solution through the iron bed 5 in the cycle the mixing tank 1—the reactor 3—mixing tank 1 is carried out continuously using the circulating pump 8 having a performance of from 100 l to 40 $m^3$ of the solution/hour (depending on the resistance of flow, as determined by the size of iron pieces and the height of bed as well as the volume of the chelating agent in the mixing tank 1) until the completion of chelation. In order to determine the progress of chelation, the content of iron dissolved in the working solution is determined. For this purpose, a sample of the working solution is taken and the iron concentration is analytically assayed. The preferred method of determination is the atomic absorption spectrometry (AAS), but any known analytical methods used for assaying iron may be employed. The complete reaction of the chelating agent and the end of the chelation is considered to be the state, in which the concentration of iron in the solution no longer rises, i.e., no further increase of this concentration in the working solution is observed analytically over a certain period of time, e.g., over a period of about 2 hours.

Alternatively, the concentration of the chelating agent can be determined by HPLC. The exemplary conditions of the HPLC measurements are as follows:

A HPLC system from Dionex (pump: P680; column thermostat: TCC-100; UV photodiode array detector: PDA-100; autosampler: ASI-100; column: C-18 Hypersil GOLD (150× 4.6 mm, particle size: 5 micrometres); temperature: 20° C.

Mobile phase: 20 ml of tert-butylammonium hydroxide+ 650 ml of water+300 ml of acetonitrile; pH value of the mixture: 6.0; eluent flow rate: 1 ml/min; analytical wavelength: 280 nm.

After completion of the chelation reaction, the solutions remaining in the flow reactor 3 and the mixing tank 1 are drained through outlets 13 and 14, respectively, and pressure-filtered using a filter 15 in order to separate any mechanical impurities. The filtrate is either the final reaction product or it is subjected to drying in order to obtain the chelate in the solid form.

Figure 2:
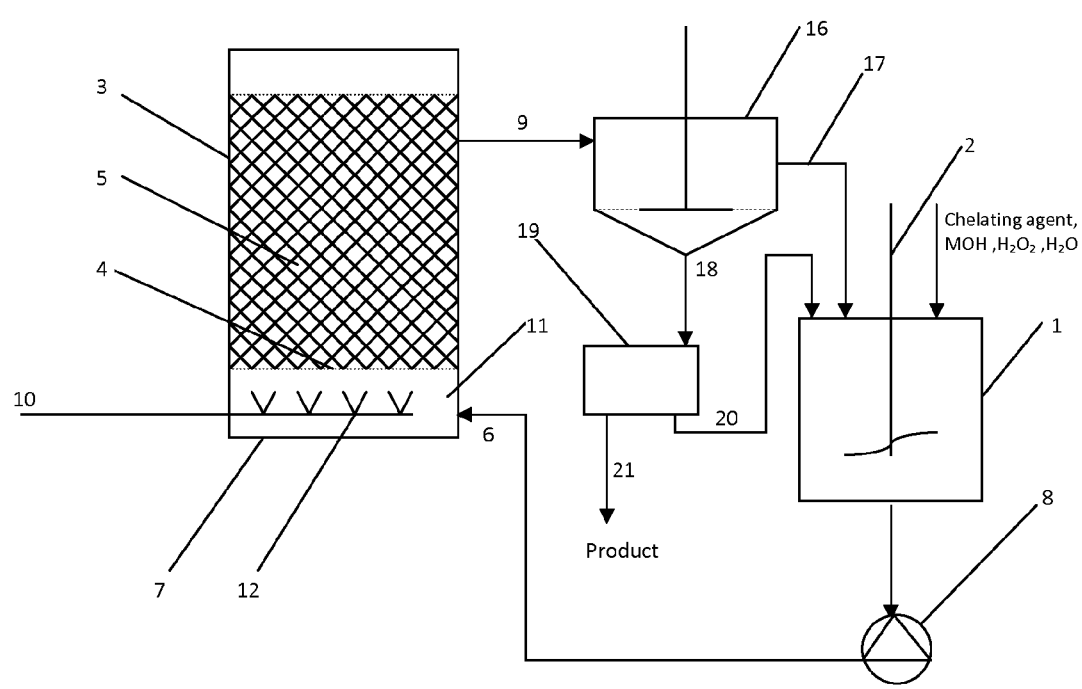
FIG. 2 presents a flowchart of the embodiment of the process according to the invention, carried out in a co-current installation, wherein the product is manufactured in the solid form.

The installation presented in FIG. 2, in which the product is manufactured in the solid form, has identical elements as the installation in FIG. 1, except that a sedimentation tank 16 (for example, a tank equipped with a stirrer) is placed between the overflow outlet 9 from the reactor 3 and the mixing tank 1 so that the gravitational flow of the working solution from the reactor 3 to the mixing tank 1 is carried out through the sedimentation tank 16. The sedimentation tank 16 is connected to the mixing tank 1 via an overflow outlet 17 located in its upper part so that it is possible to gravitationally drain the liquid from the sedimentation tank 16 into the mixing tank 1. The sedimentation tank 16 has also an outlet 18 placed at its lower part, preferably at the bottom, that is used to drain the precipitate into a separator 19 of the solid-liquid type. The separator 19 may be, for example, a pressure filter or a centrifuge. Draining the precipitate from the sedimentation tank 16 to the separator 19 is carried out periodically as the precipitate accumulates.

The process is carried out similarly to the process illustrated in FIG. 1, except that the starting concentration of the chelating agent in the circulating working solution is 12 to 25% by weight, preferably 14-17% by weight and, after obtaining the chelate-saturated solution, the process is continued until oversaturation and beginning the precipitation of the chelate insoluble in the working solution because of exceeding the solubility product, and the loss of the chelating agent in the solution, as it reacts, is successively replenished by feeding the chelating agent into the mixing tank 1.

Circulation of the working solution through the reactor 3 is carried out via the sedimentation tank 16 ad then the mixing tank 1. The chelate-containing working solution flows gravitationally from the flow reactor 3 through the overflow outlet 9 into the sedimentation tank 16. In the sedimentation tank 16, the precipitated solid iron(III) chelate is separated from the reaction mixture by sedimentation. The chelate precipitate falls to the bottom of the sedimentation tank 16, and the solution, that does not contain the suspended precipitate at all, or contains significantly less amount of the suspended precipitate, flows gravitationally from the sedimentation tank 16 into the mixing tank 1, where it is enriched by the next portion of the chelating agent and optionally by the hydrogen peroxide solution and supplied with the circulating pump 8 to the flow reactor 3 again.

The process is carried out until obtaining the iron chelate precipitate in the mixture present in the sedimentation tank 16 in the amount of 5 to 40% by volume, preferably 30 to 35% by volume, as measured by the height of the precipitate layer in the sedimentation tank 16 with relation to the upper level of the liquid in the sedimentation tank 16. This amount is determined by practical and economical reasons, i.e., the separation of the precipitate should be carried out at the optimal time intervals. If the complete saturation (i.e., consumption) of the chelating agent in the working solution and the appropriately large amount of the precipitate in the sedimentation tank 16 is not achieved yet, the next portion of the chelating agent is fed into the mixing tank 1 as well as, optionally, the next portion of the hydrogen peroxide solution. After obtaining the appropriate amount of the chelate in the solution, feeding the chelating agent into the mixing tank 1 is stopped and further circulation of the working solution is continued until the concentration of the chelating agent within the range from 0.5 to 2% by weight is obtained. A measurement of the concentration of the chelating agent is carried out by periodically sampling the mixture from the mixing tank 1 and performing a quantitative analysis for the chelating agent, preferably by HPLC. The state of complete saturation is achieved when the concentration of the chelating agent in the working solution is lowered below 1% by weight.

After completing the chelation, a mixture of the solid iron (III) chelate and the working solution present in the sedimentation tank 16 is separated in a separator 19, for example by pressure filtration or centrifugation, in order to recover the solid chelate. The eluate 20 obtained during the separation, being the saturated chelate solution in the working solution, is returned into the mixing tank 1, where it is enriched with a new portion of the chelating agent, and the whole is a raw material for the next manufacturing cycle.

The recovered precipitate 21 is dried and is the final reaction product.

The process according to the invention is further illustrated more specifically in the following non-limiting examples with the reference to FIG. 1 (for Examples 1 and 2) and to FIG. 2 (for Examples 3 to 6).

Example 1

Preparation of the Solution of Iron(III) Chelate of N,N'-di(2-hydroxybenzyl)ethylenediamine-N,N'-diacetic acid (HBED) Sodium Salt The process was carried out in the co-current installation as illustrated in FIG. 1. A solution of the chelating agent at pH=7 was prepared in the mixing tank 1 by dissolving 446.4 g (1.05 mol) of N,N'-di(2-hydroxybenzyl)ethylenediamine-N,N'-diacetic acid hydrochloride in 4000 ml of $H_2O$ and 133 ml of 50% w/w NaOH (2.54 mol). 1117.4 g of Fe (20 mol) in the form of turnings having the dimensions of 2×5×7 cm were placed in the flow reactor 3 on the baffle 4. Feeding the chelating agent solution from the mixing tank 1 to the flow reactor 3 started using the circulating pump 8. After the flow reactor 3 was filled and the solution reached the level of the overflow 9 located below the upper boundary of the iron bed 5, gravitational flow of the working solution via the overflow 9 and its recirculation into the mixing tank 1 started. Then, simultaneous feeding the hydrogen peroxide solution into the mixing tank 1 and the air into the space below the baffle 4 in the flow reactor 3 was started. The hydrogen peroxide solution in the amount of 121 ml of 50% w/w $H_2O_2$ (2.16 mol) was fed at a rate of 17 ml/h, and bubbling the air through the bed in the flow reactor was carried out at a flow rate of 0.2 l/s. The volume flow rate of the solution through the iron bed was 100 l/h. The chelation process was carried out for 12 hours. 3400 ml of the solution of FeHBEDNa at a concentration of 10.1% by weight were obtained. After drying the obtained solution in a vacuum evaporator at 80° C., 340 g of the product was obtained. The product assay was 9.0% in iron(III), 0.3% in iron(II) and 11% in chloride, by weight.

Example 2

Preparation of the Solution of Iron(III) Chelate of N,N'-di(2-hydroxy-5-methylbenzyl)ethylenediamine-N,N'-diacetic acid (HBED) Potassium Salt The process was carried out in the co-current installation as illustrated in FIG. 1. A solution of the chelating agent at pH=7 was prepared in the mixing tank 1 by dissolving 120 g (0.265 mol) of N,N'-di(2-hydroxy-5-methylbenzyl)ethylenediamine-N,N'-diacetic acid hydrochloride in 2000 ml of $H_2O$ and 50 ml of 50% w/w KOH (0.667 mol). 3 kg of iron (53.7 mol Fe) in the form of sheets having the dimensions of 1×2×0.05 cm were placed in the flow reactor 3 on the baffle 4. After filling the flow reactor 3 with the solution of the chelating agent and obtaining the recirculation of the working solution into the mixing tank 1, simultaneous feeding of the hydrogen peroxide solution into the mixing tank 1 and bubbling the air into the space 11 below the baffle 4 in the flow reactor 3 was started. The hydrogen peroxide solution in the amount of 51 ml of 50% w/w $H_2O_2$ (0.893 mol) was fed at a rate of 8.5 ml/h, and bubbling air through the bed 5 in the flow reactor was carried out at a flow rate of 0.2 l/s. The volume flow rate of the solution of the chelating agent through the iron bed 5 was 100 l/h. The chelation process was carried out for 6 hours. 2285 ml of the solution of iron(III) chelate of N,N'-di(2-hydroxy-5- methylbenzyl)ethylenediamine-N,N'-diacetic acid potassium salt at a concentration of 5.9% by weight were obtained. After drying the obtained solution in a vacuum evaporator at 80° C., 200 g of the product was obtained. The product assay was 9.0% in iron(III), 0.5% in iron(II) and 4.7% in chloride, by weight.

Example 3

Preparation of the Solid Iron(III) Chelate of N,N'-di (2-hydroxybenzyl)ethylenediamine-N,N'-diacetic acid (HBED) Ammonium Salt The process was carried out in the co-current installation as illustrated in FIG. 2. A solution of the chelating agent at pH=7 was prepared in the mixing tank 1 by dissolving 440 g (1.04 mol) of N,N'-di(2-hydroxybenzyl)ethylenediamine-N,N'-diacetic acid hydrochloride in 2200 ml of $H_2O$ and 175 ml of 25% aq. $NH_3$ (2.33 mol). A bed of 3 kg of iron (53.7 mol Fe) in the form of loosely packed rods was placed on the baffle 4 in the flow reactor 3. After filling the flow reactor 3 with the solution of the chelating agent and obtaining recirculation of the working solution into the mixing tank 1, simultaneous feeding of the hydrogen peroxide solution into the mixing tank 1 and bubbling the air into the space 11 below the baffle 4 in the flow reactor 3 was started. The hydrogen peroxide solution in an amount of 119 ml of 50% w/w $H_2O_2$ (2.13 mol) was fed at a rate of 40 ml/h, and bubbling the air through the bed 5 of the flow reactor 3 was carried out at a flow rate of 0.4 l/s. The volume flow rate of the working solution through the iron bed 5 was 300 l/h. After saturating the dissolved chelating agent with iron, an additional amounts of N,N'-di(2-hydroxybenzyl)ethylenediamine-N,N'-diacetic acid hydrochloride (273 g), ammonia (109 ml of the 25% by weight solution) and 150 ml of the 50% w/w hydrogen peroxide solution at a rate of 40 ml/h were fed into the mixing tank 1, in four portions. 3 hours after adding the last portion of the chelating agent and ammonia, monitoring of the concentration of the unreacted chelating agent in the mixing tank 1 by HPLC analysis was started. The circulation of the working solution was stopped when the concentration of the chelating agent in the working mixture dropped to 1.5% by weight. The amount of the precipitate in the sedimentation tank 16 was 28% by volume.

The precipitate separated and collected in the sedimentation tank 16 was pressure filtered and dried in a vacuum evaporator to yield 360 g of the precipitate. The obtained filtrate was returned to the mixing tank 1. The product assay was 10.0% in iron(III), 1% in iron(II) and 1.6% in chloride, by weight.

Example 4

Preparation of the Solid Iron(III) Chelate of N,N'-di (2-hydroxy-5-sulphobenzyl)ethylenediamine-N,N'-diacetic acid Sodium Salt The process was carried out in the co-current installation as illustrated in FIG. 2. Solid N,N'-di(2-hydroxy-5-sulphobenzyl)ethylenediamine-N,N'-diacetic acid (300 g, 0.547 mol) was introduced into the mixing tank 1. 1500 ml of $H_2O$ and 172 ml of 50% w/w NaOH (3.28 mol) were added, to obtain a solution of pH=7.2. 2 kg of iron in the slab form (35.8 mol Fe) were placed on the baffle 4 in the flow reactor 3. After filling the flow reactor with the solution and obtaining the recirculation of the working solution from the sedimentation tank 16 into the mixing tank 1, simultaneous feeding of the hydrogen peroxide solution into the mixing tank 1 and bubbling the air into the space 11 below the baffle 4 in the flow reactor 3 was started. The hydrogen peroxide solution in the amount of 105 ml of 50% w/w $H_2O_2$ (1.84 mol) was fed at a rate of 21 ml/h, and bubbling the air through the bed 5 in the flow reactor 3 was carried out at a flow rate of 0.2 l/s. The volume flow rate of the working solution through the iron bed 5 was 150 l/h. The concentration of the free chelating agent was monitored in the mixing tank 1 by HPLC analysis. The working cycle was terminated when the concentration of the non-chelated agent was found to be 1.2% by weight and the amount of the precipitate in the sedimentation tank 16 was 16% by volume. The precipitate separated and collected in the sedimentation tank 16 was pressure filtered and dried in a vacuum evaporator to yield 250 g of the precipitate. The filtrate was returned to the mixing tank 1. The product assay was 7.0% in iron(III) and 0.5% in iron(II), by weight.

Example 5

Preparation of the Solid Iron(III) Chelate of N,N'-di (2-hydroxy-5-carboxybenzyl)ethylenediamine-N,N'-diacetic acid Sodium Salt The process was carried out in the co-current installation as illustrated in FIG. 2. A solution of the chelating agent having pH=7 was prepared in the mixing tank 1 by dissolving 500 g (1.05 mol) of N,N'-di(2-hydroxy-5-carboxybenzyl)ethylenediamine-N,N'-diacetic acid in 2000 ml of $H_2O$ and 330 ml of 50% w/w NaOH (6.3 mol). A bed of 3 kg of iron (53.7 mol Fe) in the form of loosely distributed wires was placed in the flow reactor 3. After filling the flow reactor 3 with the solution and obtaining recirculation of the working solution into the mixing tank 1, the simultaneous feeding of the hydrogen peroxide solution into the mixing tank 1 and bubbling the air into the space 11 below the baffle 4 in the flow reactor 3 was started. The hydrogen peroxide solution in an amount of 201 ml of 50% w/w $H_2O_2$ (3.54 mol) was fed at a rate of 29 ml/h, and bubbling the air through the bed 5 of the flow reactor 3 was carried out at a flow rate of 0.3 l/s. The volume flow rate of the solution through the iron bed 5 was 200 l/h. The concentration of the free chelating agent was monitored in the mixing tank 1 by HPLC analysis. The working cycle was terminated when the concentration of the non-chelated agent was found to be 0.9% by weight and the amount of the precipitate in the sedimentation tank 16 reached 24% by volume. The precipitate collected in the sedimentation tank 16 was pressure filtered and dried in a vacuum evaporator to yield 462 g of the precipitate. The obtained filtrate was recirculated to the mixing tank 1. The product assay was 8.0% in iron(III) and 0.45% in iron(II), by weight.

Example 6

Preparation of the Solid Iron(III) Chelate of N,N'-di (2-hydroxy-5-methylbenzyl)ethylenediamine-N,N'-diacetic acid Sodium Salt The process was carried out in the co-current installation as illustrated in FIG. 2. A solution of the chelating agent at pH=7 was prepared in the mixing tank 1 by dissolving 300 g (0.662 mol) of N,N'-di(2-hydroxy-5-methylbenzyl)ethylenediamine-N,N'-diacetic acid hydrochloride in 1800 ml of $H_2O$ and 138 ml of 50% w/w NaOH (2.63 mol). A bed of 2.5 kg of iron (44.8 mol Fe) in the form of rods was placed on the perforated baffle 4 in the flow reactor 3. After filling the flow reactor with the solution and obtaining recirculation of the working solution into the mixing tank 1, the simultaneous feeding of the hydrogen peroxide solution into the mixing tank 1 and bubbling the air into the space 11 below the baffle 4 in the flow reactor 3 was started. The hydrogen peroxide solution was fed at a rate of 42 ml/h in an amount of 126 ml of 50% w/w $H_2O_2$ (2.23 mol), and bubbling the air through the bed 5 in the flow reactor 3 was carried out at a flow rate of 0.2 l/s. The volume flow rate of the working solution through the iron bed 5 was 100 l/h. The concentration of the free chelating agent was monitored in the mixing tank 1 by HPLC analysis. The working cycle was terminated when the concentration of the unreacted chelating agent in the sedimentation tank 16 was found to be 1.1% by weight and the amount of the precipitate reached 35% by volume. The precipitate separated and collected in the sedimentation tank 16 was pressure filtered and dried in a vacuum evaporator to yield 260 g of the precipitate. The filtrate was recirculated into the mixing tank 1. The product assay was 8.0% in iron(III), and 0.2% in iron(II) and 2.3% in chloride, by weight.

Example 7

Use of the Iron Chelates Obtained by the Process According to the Invention

1. Application of FeHBED for Fertilising of Soya—the Experiment Carried Out in the Plant Growth Climatic Chamber The experiment was performed using the seeds of soybean (*Glycine max* L.) var. Stine 0480. A standard seed germination procedure was followed. Before starting the experiment, the seeds were thoroughly washed with water (30 minutes). The clean seeds were placed between two sheets of a cellulose paper soaked with water. The seeds germinated over two days in a climatic chamber at a temperature of 30° C. and a humidity of 60%, without access of light. After that time, the seedlings at a similar stage of development were placed on perforated trays floating over containers containing 10 L of the diluted nutrient solution for four days, followed by next three days using a solution containing micronutrients but without iron. Composition of the nutrient solution was: 1 mM $Ca(NO_3)_2$, 0.90 mM $KNO_3$, 0.30 mM $MgSO_4$, 0.10 mM $KH_2PO_4$, 2.5 μM $MnSO_4$, 1.0 μM $CuSO_4$, 10 μM $ZnSO_4$, 1.0 μM $NiCl_2$, 1.0 μM $CoSO_4$, 115.5 μM $Na_2EDTA$, 231 μM KOH, 35 μM NaCl, 10 μM $H_3BO_3$, 0.05 μM $Na_2MoO_4$ and 0.1 mM of N-(2-hydroxyethyl)piperazine-N'-(2-ethanesulfonic acid) sodium salt (HEPES). The pH value was adjusted to 7.5 using 1M KOH. 1-litre pots were filled with soil and sand in a volume ratio of 2:1. The test plants were transplanted into the thus-prepared pots, 3 plants per each pot. The experiment was carried out with adhering to the daily cycle of plant growth: 16 h of day time (30° C., 50% humidity) and 8 h of night time (25° C., 70% humidity).

Seven days after transplanting the plants into the pots, the symptoms of chlorosis were observed. The further part of the experiment was aimed at comparison of the effectiveness of performance of FeHBED with that of the commercially available FeEDDHA. For this purpose, the solutions of FeHBED and FeEDDHA were prepared, in which the iron isotope $^{57}Fe$ was used. The concentrations of $^{57}Fe$ in the doses were 0, 1.7, 3.4, 8.4, 16.8, 25.1 and 41.9 μmol of $^{57}Fe$/kg of soil. Each dose was applied in duplicate. Additionally, a blank test (without iron) was performed for three pots.

Table 1 summarises the results of dry matter of above-ground sprouts (leaves and stems) for the plants gathered after every application of iron solutions of various concentration for two samplings.

TABLE 1

Plant dry matter (g/plant) for each application and dose in both samplings

| Dose | Sprout dry weight (g/plant) | | | | Root dry weight | |
|---|---|---|---|---|---|---|
| (μmol $^{57}Fe$/ | 1 samping | | 2 sampling | | (g/3 plants) | |
| kg of soil) | o,oEDDHA | HBED | o,oEDDHA | HBED | o,oEDDHA | HBED |
| 0 | 0.77 | 0.77 | 2.15 | 2.15 | 0.40 | 0.40 |
| 1.7 | 0.88 | 0.73 | 2.08 | 2.20 | 0.44 | 0.33 |
| 3.4 | 0.79 | 0.79 | 2.92 | 2.83 | 0.51 | 0.53 |
| 8.4 | 0.87 | 0.91 | 2.03 | 2.62 | 0.49 | 0.56 |
| 16.8 | 0.84 | 0.72 | 2.56 | 3.19 | 0.53 | 0.51 |
| 25.1 | 0.81 | 0.92 | 2.73 | 2.66 | 0.59 | 0.43 |
| 41.9 | 0.86 | 0.79 | 3.20 | 2.63 | 0.49 | 0.49 |

From comparison of the data summarised in Table 1 for HBED/$^{57}Fe^{3+}$ and o,oEDDHA/$^{57}Fe^{3+}$, it may be concluded that there is no evident difference in the sprout dry weights of the test plants.

The SPAD Index

The SPAD index (a measure of leaves greenness) was determined every two days during the whole experiment. Table 2 shows the dependence of the SPAD index (for the second and third level of foliage starting from the bottom) on the amount of iron introduced with the chelates HBED/$^{57}Fe^{3+}$ and o,oEDDHA/$^{57}Fe^{3+}$ at the end of experiment.

TABLE 2

The dependence of the SPAD index on an amount of iron in the dose at the end of experiment.

| The concentration of | $2^{nd}$ level of foliage | | $3^{rd}$ level of foliage | |
|---|---|---|---|---|
| $^{57}Fe$ in a dose [μmol of $^{57}Fe$/kg of soil] | The SPAD index for HBED | The SPAD index for EDDHA | The SPAD index for HBED | The SPAD index for EDDHA |
| 0 | 22.08 | 22.08 | 24.09 | 24.09 |
| 1.7 | 29.58 | 37.92 | 34.09 | 43.18 |
| 3.4 | 28.75 | 34.58 | 35.91 | 40.00 |
| 8.4 | 42.50 | 31.67 | 43.18 | 36.82 |
| 16.8 | 27.92 | 32.92 | 37.73 | 40.46 |
| 25.1 | 27.92 | 37.08 | 37.73 | 37.73 |
| 41.9 | 29.17 | 38.75 | 43.64 | 44.55 |

No significant differences in the values of the SPAD index were seen for both levels of foliage using both formulations, i.e., o,oEDDHA/$^{57}Fe^{3+}$ and HBED/$^{57}Fe^{3+}$.

2. Field Tests

The comparison included two chelate agents for supplementing iron deficiencies: HBED/$Fe^{3+}$ as well as the commercially available, highly purified EDDHA/$Fe^{3+}$. The studies were carried out on two fields with the soil having an alkaline pH as well as a high concentration of calcium ions. The chelates were applied directly to the soil by means of a dripper immersed in the soil.

Testing Field No. 1

10-year old nectarine trees, cultivar "Zephyr" grafted on the GF677 root stock

The chelates were applied at the following concentrations:

EDDHA/$Fe^{3+}$: high concentration (0.9 g of the chelated Fe/tree)

HBED/$Fe^{3+}$: low concentration (0.45 g of the chelated Fe/tree)

HBED/$Fe^{3+}$: high concentration (0.9 g of the chelated Fe/tree)

control trial: without Fe

The chelate solutions of various concentrations were applied in three portions (50%, 30%, and finally 20% of the whole dose, respectively) directly to the ground below the dripper.

Testing Field No. 2

7-year old trees of flat peach (*Prunus persica* var. *platycarpa*) grafted on the GF677 root stock with visible symptoms of chlorosis The chelates were applied at the following concentrations:

EDDHA/$Fe^{3+}$: high concentration (0.9 g of the chelated Fe/tree)

HBED/$Fe^{3+}$: high concentration (0.9 g of the chelated Fe/tree)

control trial: without Fe

The chelate solutions were dosed directly to the ground below the dripper. In this case, the whole dose of the chelates were applied in one portion. The symptoms of chlorosis were visible at the beginning of the experiment.

Determination of the SPAD Index

Testing Field No. 1

The SPAD index was measured approximately every two weeks: on day 14, 29, 44, 61, 88 and 99 after application of the chelates.

TABLE 3

The SPAD index of the fructifying branches of the trees for various doses of the applied chelates

| | Days after application of the chelate | | | | | |
|---|---|---|---|---|---|---|
| | 14 | 29 | 44 | 61 | 88 | 99 |
| | Control trial | | | | | |
| The SPAD index | 36.00 | 37.45 | 36.80 | 36.00 | 33.82 | 32.45 |
| | HBED/$Fe^{3+}$ 0.45 | | | | | |
| The SPAD index | 36.46 | 37.82 | 37.09 | 36.54 | 38.64 | 37.36 |
| | HBED/$Fe^{3+}$ 0.90 | | | | | |
| The SPAD index | 35.45 | 37.91 | 37.27 | 37.64 | 39.73 | 37.27 |
| | EDDHA/$Fe^{3+}$ 0.90 | | | | | |
| The SPAD index | 36.00 | 37.00 | 37.82 | 37.82 | 39.09 | 38.91 |

TABLE 4

The SPAD index of the non-fructifying branches of the trees for various doses of the applied chelates

| | Days after application of the chelate | | | | | |
|---|---|---|---|---|---|---|
| | 14 | 29 | 44 | 61 | 88 | 99 |
| | Control trial | | | | | |
| The SPAD index | 35.54 | 35.08 | 35.31 | 33.15 | 34.69 | 31.62 |
| | HBED/$Fe^{3+}$ 0.45 | | | | | |
| The SPAD index | 34.39 | 36.46 | 34.46 | 34.69 | 37.46 | 36.54 |
| | HBED/$Fe^{3+}$ 0.90 | | | | | |
| The SPAD index | 35.69 | 35.77 | 36.54 | 33.69 | 39.00 | 37.46 |
| | EDDHA/$Fe^{3+}$ 0.90 | | | | | |
| The SPAD index | 35.69 | 37.77 | 36.23 | 35.15 | 37.38 | 36.92 |

Tables 3 and 4 summarise the results of the measurement of the SPAD index for fructifying and non-fructifying branches of the trees for various doses of the applied chelates. The largest differences are seen for the control trial in both cases. The values of the SPAD index obtained for HBED/$Fe^{3+}$ and EDDHA/$Fe^{3+}$ are comparable. The chelate HBED/$Fe^{3+}$ effectively reduces the symptoms of chlorosis.

Testing Field No. 2

The samples for determination of the SPAD index of leaves were taken approximately every two weeks (on day 0, 20, 40 and 63 after application of the chelates).

TABLE 5

The variation of the SPAD index of leaves for the trees at the testing field No. 2, using various concentrations of the chelates.

| | Days after application of the chelate | | | |
|---|---|---|---|---|
| | 0 | 20 | 40 | 63 |
| | Control trial | | | |
| ΔSPAD index | 0 | −6.25 | 4.25 | 1.50 |
| | HBED/$Fe^{3+}$ 0.9 | | | |
| ΔSPAD index | 0 | 11.50 | 16.75 | 16.23 |
| | EDDHA/$Fe^{3+}$ 0.9 | | | |
| ΔSPAD index | 0 | 13.00 | 17.50 | 17.25 |

The comparison of the results summarised in Table 5 does not show any significant differences between the use of HBED/$Fe^{3+}$ and EDDHA/$Fe^{3+}$. The SPAD index increments (ΔSPAD index) for the leaves are much lower in the case of the control trial. HBED/$Fe^{3+}$ may be successfully used against iron deficiencies in soils of alkaline pH as well as of high concentration of calcium ions.

The invention claimed is:
1. A process for the preparation of iron(III) chelates of N,N'-di(2-hydroxybenzyl)ethylenediamine-N,N'-diacetic acid and its derivatives of the formula (I)

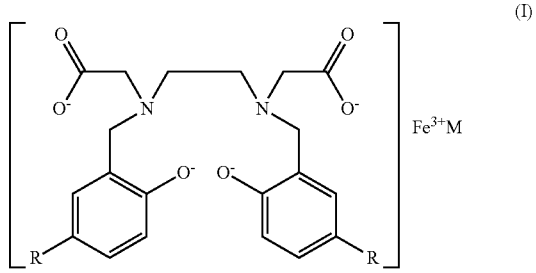

wherein both R substituents have the same meaning and represent H, $C_1$-$C_4$ alkyl, $CH_2OH$, $SO_3M$ or COOM, and M is a sodium, potassium or ammonium cation, characterised in that a starting aqueous solution of the chelating agent of the formula (II)

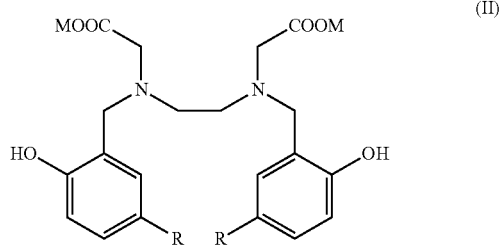

wherein R and M are as defined above is prepared,
the aqueous solution is contacted with metallic iron by the circulation of said aqueous solution through the bed of pieces of metallic iron in a flow reactor while simultaneously blowing air or oxygen through the aqueous solution of the chelating agent in the flow reactor, and a hydrogen peroxide solution is optionally added to the aqueous solution of the chelating agent received from the flow reactor and before returning it to the flow reactor, whereby said circulating aqueous solution is continuously enriched with the iron chelate of the formula (I).

2. The process according to claim 1 wherein the hydrogen peroxide solution is added to the aqueous solution of the chelating agent received from the flow reactor and before returning it to the flow reactor.

3. The process according to claim 2 wherein a concentration of the hydrogen peroxide solution is in the range of 3 to 60% by weight.

4. The process according to claim 3 wherein the concentration of the hydrogen peroxide solution is 50% by weight.

5. The process according to claim 1 wherein a concentration of the chelating agent in the starting aqueous solution is in the range of 1 to 12% by weight and the circulation of the aqueous solution of the chelating agent is carried out until complete conversion of the chelating agent, whereby the aqueous solution of the iron chelate is obtained as a final product.

6. The process according to claim 5 wherein the final aqueous solution is further concentrated to a solid product.

7. The process according to claim 1 wherein a concentration of the chelating agent in the starting aqueous solution is in the range of 12 to 25% by weight, circulation of the aqueous solution is carried out until oversaturation of the circulating aqueous solution with the iron chelate, whereby a solid chelate precipitates from the circulating solution received from the flow reactor and is separated from the circulating aqueous solution in a sedimentation tank and collected therein, and wherein the circulating aqueous solution before returning it to the flow reactor is optionally fed with further portion of the chelating agent, and the collected solid iron chelate precipitate is periodically recovered from the sedimentation tank.

8. The process according to claim 7 wherein the concentration of the chelating agent in the starting solution is in the range of 14 to 17% by weight.

9. The process according to claim 7 wherein the circulation of the aqueous solution and the optional feeding with the chelating agent are carried out until the amount of the separated and collected solid iron chelate precipitate is equal to 5 to 40% of the volume of the sedimentation tank and the chelate is recovered in the form of a solid product.

10. The process according to claim 9 wherein after obtaining 5 to 40% of the volume of the solid iron chelate precipitate separated and collected in the sedimentation tank the circulation of the aqueous solution is further carried out without adding further portion of the chelating agent until the concentration of the chelating agent in the circulating solution is below 2% by weight.

11. The process according to claim 7 wherein the periodical recovery of the collected solid iron chelate precipitate from the sedimentation tank is carried out by filtration or centrifugation.

12. The process according to claim 1 wherein the aqueous solution of the chelating agent is prepared in a mixing tank by dissolving in water:
a solid chelating agent of the formula (II), wherein M is a sodium, potassium or ammonium cation, or
a hydrochloride or sulphate of the chelating agent of the formula (II), wherein M is a hydrogen cation, and the stoichiometric amount of sodium, potassium or ammonium hydroxide.

13. The process according to claim 12 wherein the hydrogen peroxide solution is added to the aqueous solution of the chelating agent received from the flow reactor and before returning it to the flow reactor.

14. The process according to claim 13 wherein a concentration of the hydrogen peroxide solution is in the range of 3 to 60% by weight.

15. The process according to claim 14 wherein the concentration of the hydrogen peroxide solution is 50% by weight.

16. The process according to claim 12 wherein a concentration of the chelating agent in the starting aqueous solution is in the range of 1 to 12% by weight and the circulation of the aqueous solution of the chelating agent is carried out until complete conversion of the chelating agent, whereby the aqueous solution of the iron chelate is obtained as a final product.

17. The process according to claim 16 wherein the final aqueous solution is further concentrated to a solid product.

18. The process according to claim 12 wherein a concentration of the chelating agent in the starting aqueous solution is in the range of 12 to 25% by weight, circulation of the aqueous solution is carried out until oversaturation of the circulating aqueous solution with the iron chelate, whereby a solid chelate precipitates from the circulating solution received from the flow reactor and is separated from the circulating aqueous solution in a sedimentation tank and collected therein, and wherein the circulating aqueous solution before returning it to the flow reactor is optionally fed with further portion of the chelating agent, and the collected solid iron chelate precipitate is periodically recovered from the sedimentation tank.

19. The process according to claim 18 wherein the concentration of the chelating agent in the starting solution is in the range of 14 to 17% by weight.

20. The process according to claim 18 wherein the circulation of the aqueous solution and the optional feeding with the chelating agent are carried out until the amount of the separated and collected solid iron chelate precipitate is equal to 5 to 40% of the volume of the sedimentation tank and the chelate is recovered in the form of a solid product.

21. The process according to claim 20 wherein after obtaining 5 to 40% of the volume of the solid iron chelate precipitate separated and collected in the sedimentation tank the circulation of the aqueous solution is further carried out without adding further portion of the chelating agent until the concentration of the chelating agent in the circulating solution is below 2% by weight.

22. The process according to claim 18 wherein the periodical recovery of the collected solid iron chelate precipitate from the sedimentation tank is carried out by filtration or centrifugation.

23. The process according to claim 12 wherein the aqueous solution of the chelating agent is prepared in a mixing tank by dissolving in water:
   a solid chelating agent of the formula (II), wherein M is a sodium, potassium or ammonium cation, or
   a hydrochloride or sulphate of the chelating agent of the formula (II), wherein M is a hydrogen cation, and the stoichiometric amount of sodium, potassium or ammonium hydroxide.

* * * * *